(12) United States Patent
Ishikawa

(10) Patent No.: US 9,561,349 B2
(45) Date of Patent: Feb. 7, 2017

(54) CATHETER

(71) Applicant: OLYMPUS CORPORATION, Tokyo (JP)

(72) Inventor: Masahiro Ishikawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/789,387

(22) Filed: Jul. 1, 2015

(65) Prior Publication Data

US 2016/0184555 A1 Jun. 30, 2016

Related U.S. Application Data

(63) Continuation of application No. PCT/JP2014/064298, filed on May 29, 2014.

(Continued)

(51) Int. Cl.
*A61M 25/00* (2006.01)
*A61M 25/09* (2006.01)
(Continued)

(52) U.S. Cl.
CPC ......... *A61M 25/09041* (2013.01); *A61L 29/04* (2013.01); *A61L 29/14* (2013.01);
(Continued)

(58) Field of Classification Search
CPC ................ A61M 25/0045; A61M 25/0054; A61M 25/09041
See application file for complete search history.

(56) References Cited

U.S. PATENT DOCUMENTS 4,899,787 A * 2/1990 Ouchi .................. A61B 1/0055
138/131
5,222,949 A * 6/1993 Kaldany ............... A61L 29/042
600/433

(Continued)

FOREIGN PATENT DOCUMENTS

JP    S62-84768 A    4/1987
JP    H08-317969 A   12/1996
(Continued)

OTHER PUBLICATIONS

Sep. 2, 2014 Search Report issued in International Patent Application No. PCT/JP2014/064298.

(Continued)

*Primary Examiner* — Aarti B Berdichevsky
(74) *Attorney, Agent, or Firm* — Oliff PLC

(57) ABSTRACT

A catheter includes an elongate member configured to have a longitudinal axis and formed of a thermoplastic resin; an elongate guide wire holder section configured to include a cavity into which a guide wire is insertable at an interior of the elongate member; a cross-linked section configured to have a high cross-linked section and a low cross-linked section which is adjacent to the high cross-linked section in a radial direction of the elongate member and in which the cross-linking degree is relatively lower than that of the high cross-linked section; and an opening section configured to communicate with the cavity of the guide wire holder and an outer circumferential surface of the guide wire holder in the low cross-linked section of the cross-linked section and formed in a slit shape along the longitudinal axis of the guide wire holder.

8 Claims, 11 Drawing Sheets

Related U.S. Application Data

(60) Provisional application No. 61/860,383, filed on Jul. 31, 2013.

(51) Int. Cl.
*A61L 29/04* (2006.01)
*A61L 29/14* (2006.01)

(52) U.S. Cl.
CPC .... *A61M 25/0026* (2013.01); *A61M 25/0043* (2013.01); *A61M 2025/09116* (2013.01)

(56) References Cited

U.S. PATENT DOCUMENTS

| | | | | |
|---|---|---|---|---|
| 5,397,306 | A * | 3/1995 | Nobuyoshi | A61M 25/0045 604/103.14 |
| 6,261,260 | B1 * | 7/2001 | Maki | A61L 29/04 428/35.5 |
| 6,945,970 | B2 * | 9/2005 | Pepin | A61L 29/085 138/134 |
| 8,696,657 | B2 * | 4/2014 | Matsunaga | A61B 18/1492 606/28 |
| 2010/0160727 | A1 | 6/2010 | Matsunaga et al. | |
| 2011/0295217 | A1 * | 12/2011 | Tanaka | A61B 1/0011 604/264 |

FOREIGN PATENT DOCUMENTS

| | | |
|---|---|---|
| JP | H09-512445 A | 12/1997 |
| JP | H10-286309 A | 10/1998 |
| JP | 4443631 B2 | 3/2010 |
| JP | 4610902 B2 | 1/2011 |
| JP | 4624483 B2 | 2/2011 |
| WO | 95/28982 A1 | 11/1995 |
| WO | 98/10821 A1 | 3/1998 |
| WO | 03/061456 A2 | 7/2003 |

OTHER PUBLICATIONS

Mar. 27, 2015 Office Action issued in Japanes Patent Application No. 2014-561209.

* cited by examiner

CATHETER

This application is a continuation application based on a PCT International Application No. PCT/JP2014/064298, filed on May 29, 2014, whose priority is claimed on U.S. Provisional Patent Application No. 61/860,383, filed on Jul. 31, 2013, the contents of both of the PCT International Application and the U.S. Provisional Patent Application are incorporated herein by reference.

BACKGROUND OF THE INVENTION

Field of the Invention
The present invention relates to a medical catheter.
Description of Related Art
Catheters used in combination with a guide wire are known. For example, a catheter having a guide wire lumen in a direction of a longitudinal axis thereof and an opening in an outer wall thereof is disclosed in Japanese Patent No. 4443631.

In such a catheter, the guide wire is inserted into a biliary duct or a pancreatic duct from a duodenal papilla via a channel of an endoscope. Also, a grip-side end of the guide wire is inserted into a guide wire opening of a distal end of the catheter. When the guide wire approaches the opening, the catheter is bent, and thereby the guide wire can be sent out of the catheter via the opening. In this state, the catheter is inserted into the channel of the endoscope, and is guided to the biliary duct or the pancreatic duct by the guide wire.

SUMMARY OF THE INVENTION

According to a first aspect of the present invention, a catheter includes an elongate member configured to have a longitudinal axis and formed of a thermoplastic resin; an elongate guide wire holder section configured to include a cavity into which a guide wire is insertable at an interior of the elongate member; a cross-linked section configured to have a high cross-linked section in which a cross-linking degree of the thermoplastic resin is relatively high and a low cross-linked section which is adjacent to the high cross-linked section in a radial direction of the elongate member and in which the cross-linking degree is relatively lower than that of the high cross-linked section and to run from a distal end to a proximal end of the guide wire holder; and an opening section configured to communicate with the cavity of the guide wire holder and an outer circumferential surface of the guide wire holder in the low cross-linked section of the cross-linked section and formed in a slit shape along the longitudinal axis of the guide wire holder.

According to a second aspect of the present invention, the catheter according to the first aspect may further include a guide wire lumen formed along the longitudinal axis to insert the guide wire into the elongate member at a distal end portion of the elongate member; and an edge section configured to communicate with the guide wire lumen, disposed at a proximal end of the guide wire lumen, configured to form the opening section of the slit shape along the longitudinal axis in an outer circumferential surface of the elongate member, continuously formed along the longitudinal axis, and configured to protrude from a position facing an edge of the opening section toward a mutually approaching direction, wherein a width of the opening section may be smaller than or equal to a diameter of the guide wire in a state in which no external force is applied to the edge section, and may be passively changed by elastic deformation of the thermoplastic resin of the edge section, and a portion located at a side opposite to the opening section in the radial direction of the elongate member may be configured in such a manner that the cross-linking degree of the thermoplastic resin is higher than that of the edge section.

According to a third aspect of the present invention, in the catheter according to the second aspect, a protecting section in which a crosslinking agent is cross-linked and which has a higher hardness than when the crosslinking agent is not cross-linked may be provided adjacent to a boundary between the guide wire lumen and the opening section in a direction of the longitudinal axis of the elongate member.

According to a fourth aspect of the present invention, in the catheter according to the third aspect, the protecting section may be provided to be connected from a position of a distal end side of the elongate member relative to the boundary between the guide wire lumen and the opening section to a position of a proximal end side of the elongate member relative to the boundary.

According to a fifth aspect of the present invention, in the catheter according to the second aspect, the edge section that is within a range from the proximal end of the guide wire lumen to a proximal end side of the elongate member by a predetermined length may be configured in such a manner that the high cross-linked section and the low cross-linked section are alternately disposed in the direction of the longitudinal axis of the elongate member.

According to a sixth aspect of the present invention, in the catheter according to the second aspect, when the elongate member is viewed in a direction of a straight line that is perpendicular to a straight line connecting the opening section and a side opposite to the opening section in the radial direction of the elongate member and extends in the radial direction of the elongate member, a projected area of a portion at which the thermoplastic resin is cross-linked at the edge section may be smaller than that of a portion at which the thermoplastic resin is cross-linked except the edge section, within a range in which the edge section is provided in the direction of the longitudinal axis of the elongate member.

According to a seventh aspect of the present invention, in the catheter according to the second aspect, regions in which a crosslinking agent is uncross-linked throughout a circumference of the elongate member in a circumferential direction of the elongate member and which have a length in the direction of the longitudinal axis of the elongate member, and regions in which the elongate member is cross-linked may be alternately provided in the direction of the longitudinal axis at a part of a distal end portion of the elongate member within a range in which the slit section is provided in the direction of the longitudinal axis of the elongate member.

According to an eighth aspect of the present invention, in the catheter according to the first aspect, the elongate member may include a distal end section that is adjacent to the opening section and runs from a distal end edge of the opening section to a proximal side; the distal end section may have the guide wire lumen that communicates with the guide wire holder and extends from the distal end edge of the opening section to the proximal side; and the high cross-linked section may be formed at the distal end edge of the opening section and adjacent to the distal end edge of the opening section

DETAILED DESCRIPTION OF THE INVENTION

First Embodiment

Figure 1:
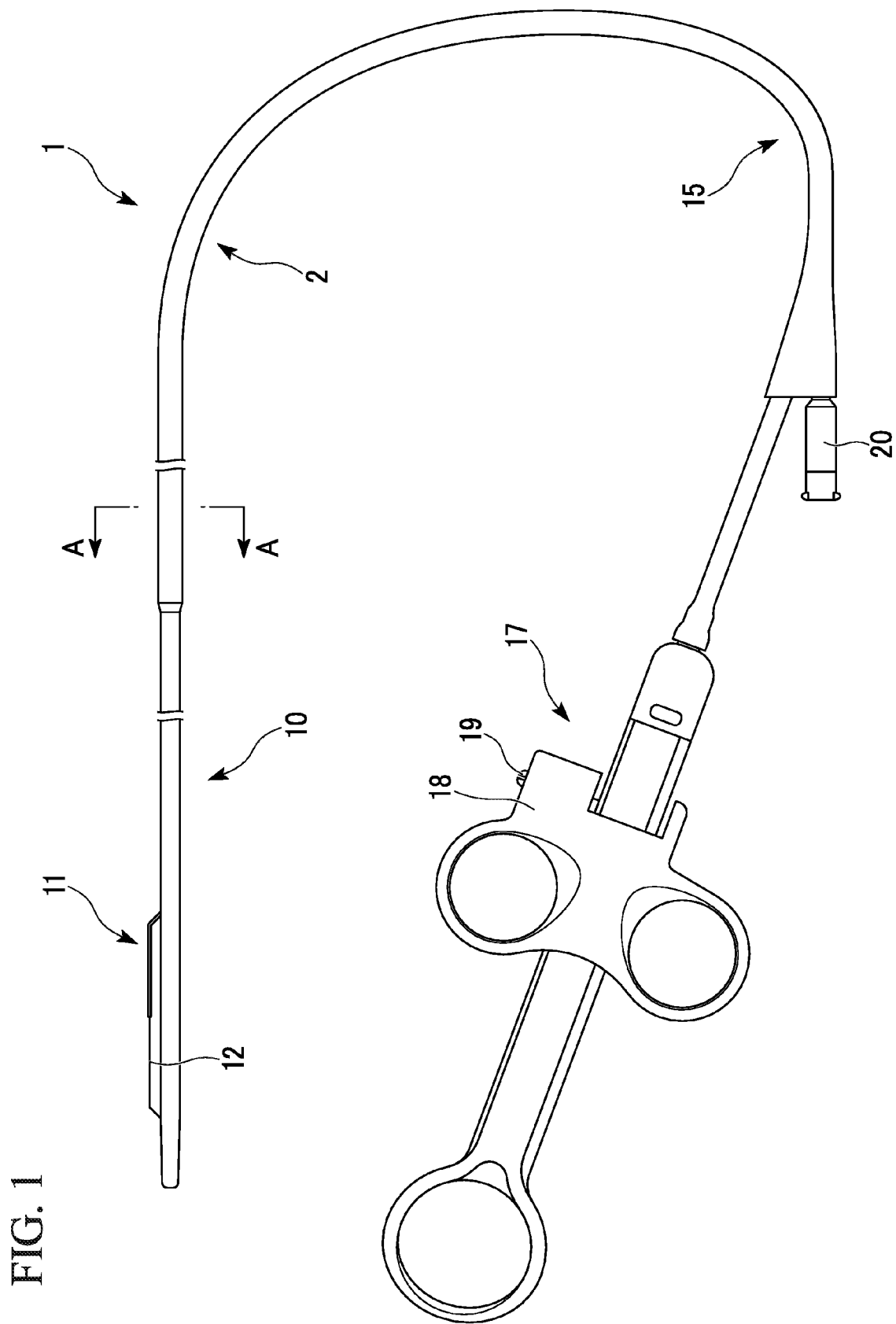
FIG. 1 is a side view showing a catheter according to a first embodiment of the present invention.
Figure 2:
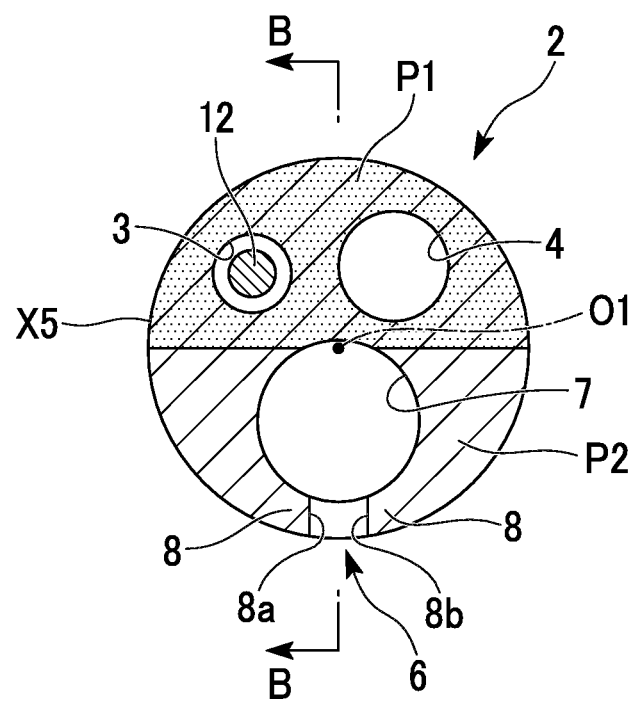
FIG. 2 is a sectional view taken along line A-A of FIG. 1.
Figure 3:
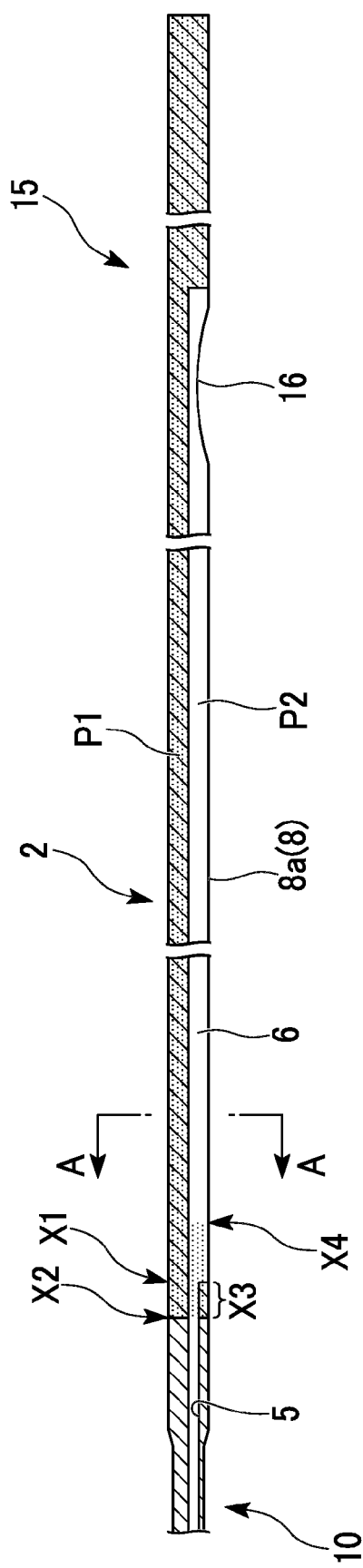
FIG. 3 is a sectional view taken along line B-B of FIG. 2.
Figure 4:
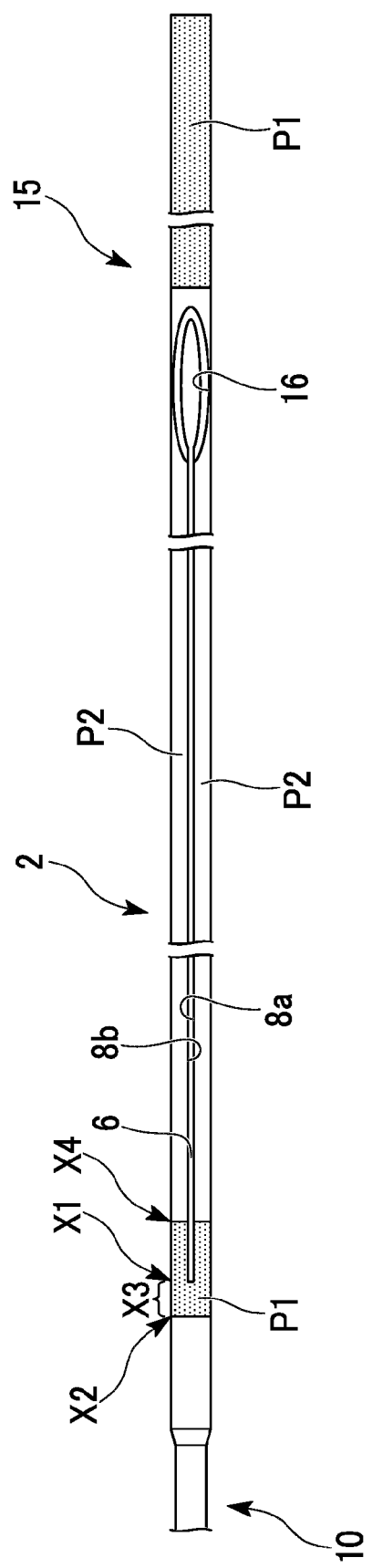
FIG. 4 is a bottom view showing a part of the catheter according to the first embodiment of the present invention.

A first embodiment of a catheter 1 of the present invention will be described. FIG. 1 is a side view showing a catheter 1 according to a first embodiment of the present invention. FIG. 2 is a sectional view taken along line A-A of FIG. 1. FIG. 3 is a sectional view taken along line B-B of FIG. 2. FIG. 4 is a bottom view showing a part of the catheter 1 according to the first embodiment of the present invention.

The catheter 1 of the present embodiment shown in FIG. 1 is a catheter used in combination with a known endoscope and a known medical guide catheter in order to make an incision in a duodenal papilla.

As shown in FIG. 1, the catheter 1 has a elongate member 2, a distal end section 10 disposed at a distal end of the elongate member 2, and a grip section 15 disposed at a proximal end of the elongate member 2.

The elongate member 2 shown in FIGS. 1 and 2 is formed of a thermoplastic resin. In the present embodiment, the thermoplastic resin applied to the elongate member 2 is cross-linked, thereby making it possible to enhance hardness (rigidity). For example, the elongate member 2 is a long member formed of a thermoplastic resin containing a cross-linking agent that can be cross-linked by ionizing radiation. Alternatively, the elongate member 2 may be a long member formed of a thermoplastic resin containing a crosslinking agent that can be cross-linked by heat.

The elongate member 2 has a longitudinal axis O1. A knife wire lumen 3, a solution sending lumen 4, a guide wire lumen 5, and a slit section 6 are formed inside the elongate member 2 to extend in parallel to the longitudinal axis O1.

A distal end of the knife wire lumen 3 further extends from a distal end of the elongate member 2 to a distal end portion of the distal end section 10. The distal end of the knife wire lumen 3 is open to an outer circumferential surface of the distal end section 10 at an incision section 11 to be described below. A proximal end of the knife wire lumen 3 extends up to the grip section 15.

A distal end of the solution sending lumen 4 further extends from the distal end of the elongate member 2 to a distal end of the distal end section 10. The distal end of the solution sending lumen 4 is open at the distal end of the distal end section 10. A proximal end of the solution sending lumen 4 extends up to the grip section 15.

As shown in FIGS. 2 and 3, the guide wire lumen 5 is open at the distal end of the distal end section 10 through a part of a distal end portion of the elongate member 2 and an interior of the distal end section 10. The guide wire lumen 5 has a cavity of such a size that a guide wire can freely move back and forth in a central axis direction thereof.

As shown in FIGS. 2 and 3, the slit section 6 has a guide wire holder 7 and an edge section 8. The guide wire holder 7 has a cavity through which the guide wire can freely move back and forth in the central axis direction thereof. The edge section 8 forms an opening for attaching the guide wire to or detaching it from the slit section 6. The edge section 8 is a region corresponding to an edge section of an opening of the slit section 6 in a cross section perpendicular to the longitudinal axis O1 of the elongate member 2. In the cross section perpendicular to the longitudinal axis O1 of the elongate member 2, the edge section 8 has a first edge section 8a and a second edge section 8b. The first edge section 8a and the second edge section 8b are disposed away from each other across the opening of the slit section 6. Both the first edge section 8a and the second edge section 8b extend in a direction in which the longitudinal axis O1 of the elongate member 2 extends.

The distal end section 10 shown in FIGS. 1 and 3 is a portion located at a distal end portion relative to a position of a distal end of the slit section 6 in the catheter 1. The distal end section 10 has a distal end portion of the knife wire lumen 3, a distal end portion of the solution sending lumen 4, a distal end portion of the guide wire lumen 5, and the incision section 11 for incising the duodenal papilla.

The incision section 11 shown in FIG. 1 has a knife wire 12. A high-frequency electric current for incising the duodenal papilla flows through the knife wire 12.

The knife wire 12 is lengthened and provided in a direction of the longitudinal axis O1 of the distal end section 10 at the distal end portion of the distal end section 10. A distal end of the knife wire 12 is fixed in the knife wire lumen 3 at a part of the distal end portion of the distal end section 10. A proximal end of the knife wire 12 is disposed to extend up to the grip section 15 through the knife wire lumen 3. The knife wire 12 can be moved back and forth in the knife wire lumen 3 in a central axis direction thereof. For this reason, when the knife wire 12 is pulled toward the proximal end thereof at the grip section 15, the distal end of the knife wire 12 pulls the distal end of the distal end section 10 toward the proximal end of the knife wire 12, and thereby the distal end section 10 is bent.

A portion at which the knife wire 12 is exposed to the outside of the distal end section 10 at the distal end side of the knife wire 12 is a portion that comes into contact with the duodenal papilla in order to incise the duodenal papilla. To allow this portion to flow the high-frequency electric current, a conductor is exposed. When the distal end section 10 is in a bent state, a portion pulled into the knife wire lumen 3 and a portion located at the proximal end side relative to the pulled portion are covered with an insulator.

As shown in FIGS. 3 and 4, the grip section 15 has a proximal end opening 16 of the slit section 6. An operating section 17 and a proximal end connector 20 of the solution sending lumen 4 are mounted on the grip section 15. The operating section 17 is provided to move the knife wire 12 back and forth.

The proximal end opening 16 of the slit section 6 has a shape in which the edge section 8 is cut out such that the guide wire holder 7 is exposed.

The operating section 17 shown in FIG. 1 has a slider 18 and a plug 19. The slider 18 moves the knife wire 12 back and forth relative to the knife wire lumen 3. The plug 19 is provided to flow the high-frequency electric current through the knife wire 12.

Next, a cross-linked state of a crosslinking agent in the catheter 1 of the present embodiment will be described in detail.

The catheter 1 of the present embodiment is configured in consideration of satisfying all of hardness for efficiently transmitting a pressing force from the grip section 15 toward the distal end section 10, flexibility for facilitating attaching the guide wire to or detaching it from the slit section 6, and durability against rough manipulation when the guide wire is detached from the slit section 6. The catheter 1 of the present embodiment has a predetermined cross-linked pattern with a cross-linked section P1 and an uncross-linked section P2 in the elongate member 2, the distal end section 10, and the grip section 15.

A position of the cross-linked section P1 will be specifically described.

First, as shown in FIG. 3, the distal end section 10 is cross-linked in a range from a boundary X1 between the guide wire lumen 5 and the slit section 6 to a position X2 of the distal end side by a predetermined distance. To be specific, in the distal end section 10, a portion X3 adjacent to the distal end side of the opening of the slit section 6 in the direction of the longitudinal axis O1 of the elongate member 2 is at least cross-linked. Thereby, when manipulation of detaching the guide wire from the slit section 6 through the opening of the slit section 6 toward a radial outer side of the elongate member 2 is performed, it is possible to prevent the distal end section 10 from being torn by the guide wire eating into the distal end section 10 due to a force applied to the guide wire. The portion X3 adjacent to the distal end side of the opening of the slit section 6 is an approximately disc-shaped or column-shaped region having a thickness in the direction of the longitudinal axis O1 of the elongate member 2. If the thickness dimension in the direction of the longitudinal axis O1 is increased at the portion X3 adjacent to the distal end side of the opening of the slit section 6, an amount by which the distal end section 10 is torn when the guide wire eats into the distal end section 10 is reduced. Alternatively, the thickness dimension of the portion X3 adjacent to the distal end side of the opening of the slit section 6 in the direction of the longitudinal axis O1 may be set in consideration of the flexibility required of the portion X3.

In the present embodiment, the entire circumference of the distal end section 10 in the range from the boundary X1 between the guide wire lumen 5 and the slit section 6 to the distal end side by the predetermined distance is cross-linked, and an interior of the distal end section 10 in the corresponding range is also cross-linked together.

Next, the elongate member 2 is cross-linked from the boundary X1 between the guide wire lumen 5 and the slit section 6 to a position X4 of the proximal end side by a predetermined distance. To be specific, in the elongate member 2, the entire circumference of the elongate member 2 in the range from the boundary X1 between the guide wire lumen 5 and the slit section 6 to a position X4 of the proximal end side by the predetermined distance is cross-linked, and an interior of the elongate member 2 in the corresponding range is also cross-linked together. The interior of the elongate member 2 refers to a region that is located on an outer circumferential surface of the elongate member 2 in a cross section perpendicular to the longitudinal axis O1 of the elongate member 2 and at an inner side relative to the corresponding outer circumferential surface, and simultaneously a region from which the cavity occurring in the elongate member 2 due to the slit section 6 is detached.

In the present embodiment, the entire region from the position X2 of the distal end side relative to the boundary X1 to the position X4 of the proximal end side relative to the boundary X1 is cross-linked to cover the boundary X1 between the guide wire lumen 5 and the slit section 6.

Further, as shown in FIG. 2, a portion X5 located on the opposite side of the opening of the slit section 6 across the longitudinal axis O1 in a radial direction of the elongate member 2 is cross-linked. As the portion X5 is cross-linked, the elongate member 2 has a hardness by which the amount of force for the manipulation of moving back and forth along the longitudinal axis O1 of the elongate member 2 or an amount of force for of the manipulation of rotating about the longitudinal axis O1 of the elongate member 2 can be efficiently transmitted from the grip section 15 to the distal end section 10. Herein, the hardness of the elongate member 2 refers to an elastic restoring force against a bending force by which the longitudinal axis O1 of the elongate member 2 is bent, an elastic restoring force against a force by which the elongate member 2 is twisted about the longitudinal axis O1 of the elongate member 2, and an elastic restoring force by which a shape of the cross section perpendicular to the longitudinal axis O1 of the elongate member 2 is maintained in the elongate member 2. That is, the elongate member 2 has rigidity capable of properly transmitting the amount of the force for the manipulation while having flexibility to some extent. It is preferable that the elongate member 2 is plastically deformable, for instance, in the track of a bent shape of a treatment tool channel of an endoscope rather than having high hardness but being brittle.

The grip section 15 is cross-linked on the entire region from the proximal end of the proximal end opening 16 of the slit section 6 to the proximal end side again.

These constitute the cross-linked section P1 in the present embodiment.

Next, a specific position of the uncross-linked section P2 in the present embodiment will be described.

The entire region covering the distal end side of the elongate member 2 which is farther than the position X2 of the distal end side by a predetermined distance from the boundary X1 between the guide wire lumen 5 and the slit section 6 is in an uncross-linked state.

The edge section 8 is in an uncross-linked state.

These constitute the uncross-linked section P2 in the present embodiment.

The edge section 8 contains a crosslinking agent, but it is not positively cross-linked. That is, the a portion X5 located on the opposite side of the opening of the slit section 6 across the longitudinal axis O1 in the radial direction of the elongate member 2 has a higher cross-linking degree than the edge section 8, and thus has higher hardness than the edge section 8. Thereby, the portion located on the opposite side of the opening of the slit section 6 in the radial direction of the elongate member 2 can prevent buckling of the elongate member 2 against a pressing force directed from the grip section 15 toward the distal end section 10 and efficiently transmit the pressing force. The edge section 8 can be smoothly subjected to elastic deformation, and the guide wire can be easily attached and detached.

Instead of having the uncross-linked section P2, a low cross-linked section in which the cross-linking degree is relatively low compared to the cross-linked section P1 may be provided.

Next, an operation of the catheter 1 according to the present embodiment will be described.

The catheter 1 according to the present embodiment is continuously cross-linked in the range from the proximal end of the grip section 15 to the distal end of the elongate member 2. For this reason, even if a pressing force for pressing the catheter 1 of the present embodiment into the treatment tool channel of the endoscope is applied to the grip section 15 and the elongate member 2, the grip section 15 and the elongate member 2 rarely buckle.

In the catheter 1 according to the present embodiment, the entire region covering the distal end side of the elongate member 2 which is farther than the position X2 of the distal end side by the predetermined distance from the boundary X1 between the guide wire lumen 5 and the slit section 6, and the edge section 8 are in an uncross-linked state.

For this reason, in the distal end section 10, the distal end side of the elongate member 2 with respect to the position X2 of the distal end side from the boundary X1 between the guide wire lumen 5 and the slit section 6 by the predetermined distance is easily deformed in a bent shape by a pulling operation of the knife wire 12.

Further, since the edge section 8 is in an uncross-linked state, when the guide wire is brought in the slit section 6 through the opening or is detached from the slit section 6, the edge section 8 is smoothly subjected to elastic deformation. Thus, the guide wire is easily attached and detached.

In addition, in the catheter 1 used together with the guide wire, the guide wire may be attached to or detached from the catheter during treatment for a patient. Especially, when the catheter 1 and the guide wire are separated, rough manipulation is sometimes performed for the purpose of reducing a treatment time. At this time, the distal end (portion X3 adjacent to the distal end side of the opening of the slit section 6) of the slit section 6 is strongly pressed against the guide wire. In the catheter 1 according to the present embodiment, the distal end of the slit section 6 is further reinforced by cross-linking, and is unlikely to tear.

To be more specific, in the present embodiment, the entire region from the position X2 of the distal end side relative to the boundary X1 to the position X4 of the proximal end side relative to the boundary X1 is cross-linked to cover the boundary X1 between the guide wire lumen 5 and the slit section 6. The cross-linking in the region of the distal end side relative to the boundary X1 prevents the catheter 1 from being torn toward the distal end side in the direction of the longitudinal axis O1 of the elongate member 2 when the guide wire is pressed against the portion of the boundary X1 from the boundary X1 toward the distal end side in order to separate the catheter 1 and the guide wire.

Also, when the guide wire is detached by the rough manipulation, a force is not necessarily applied only toward the distal end side from the boundary X1 along the longitudinal axis O1, and a force may be applied forward obliquely from the boundary X1. In the present embodiment, the entire region from the position X2 of the distal end side relative to the boundary X1 to the position X4 of the proximal end side relative to the boundary X1 is cross-linked. Thereby, the portion cross-linked from the boundary X1 to the position X4 prevents the edge section 8 from being torn at the boundary X1 in a circumferential direction.

Thereby, when the manipulation of detaching the guide wire from the slit section 6 toward the radial outer side of the elongate member 2 is performed, the catheter 1 can be prevented from being torn from the boundary portion between the elongate member 2 and the distal end section 10 by the force applied to the guide wire and the elongate member 2.

Second Embodiment

Figure 5:
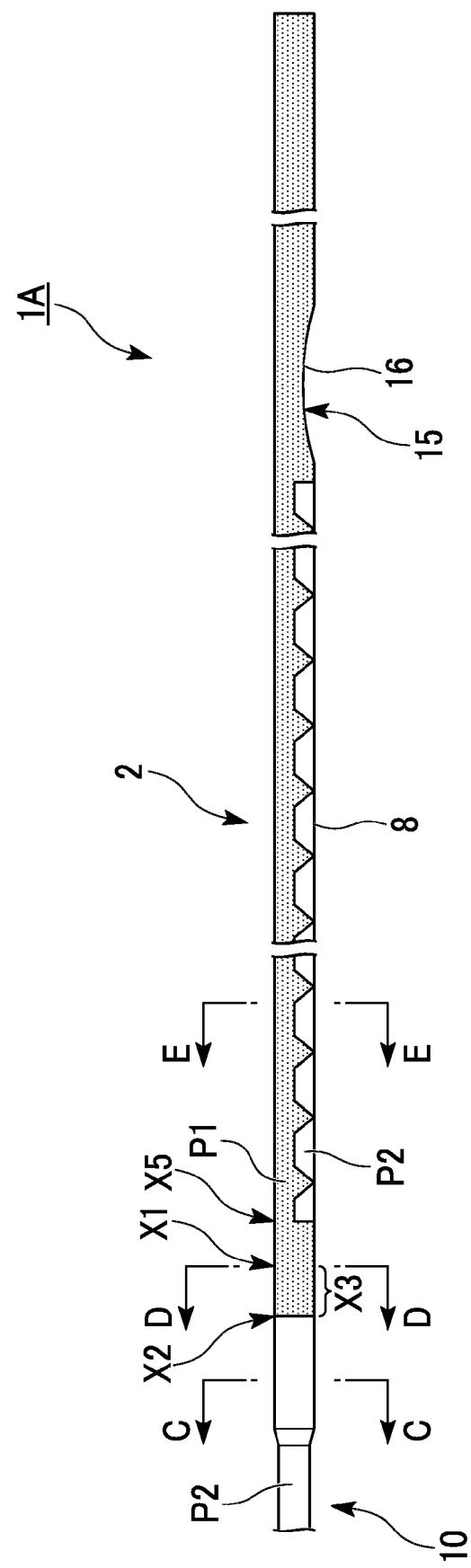
FIG. 5 is a side view showing a catheter according to a second embodiment of the present invention.
Figure 6:
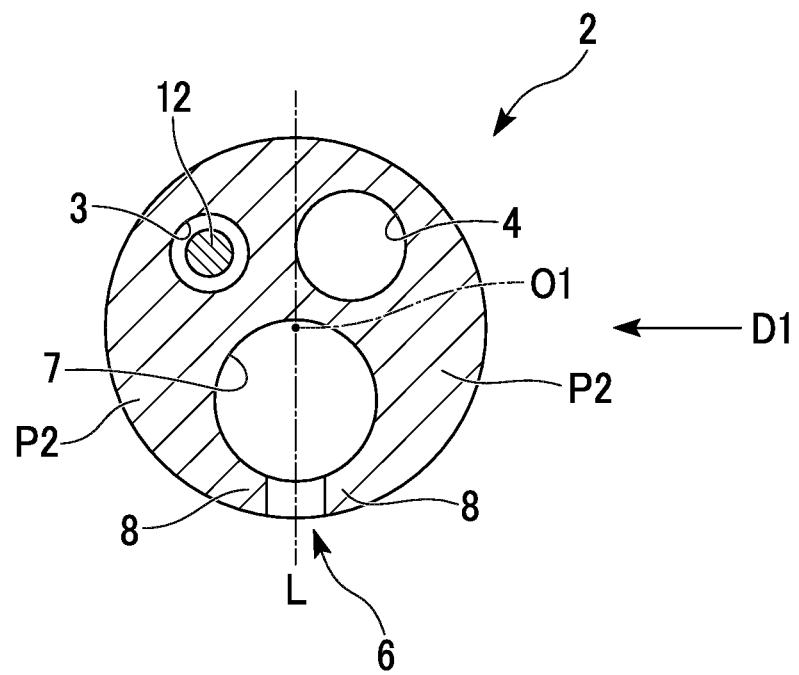
FIG. 6 is a sectional view taken along line C-C of FIG. 5.
Figure 7:
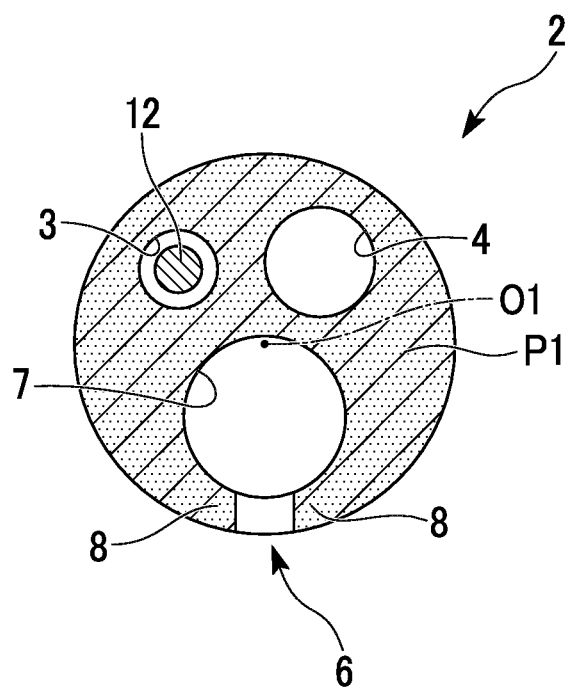
FIG. 7 is a sectional view taken along line D-D of FIG. 5.
Figure 8:
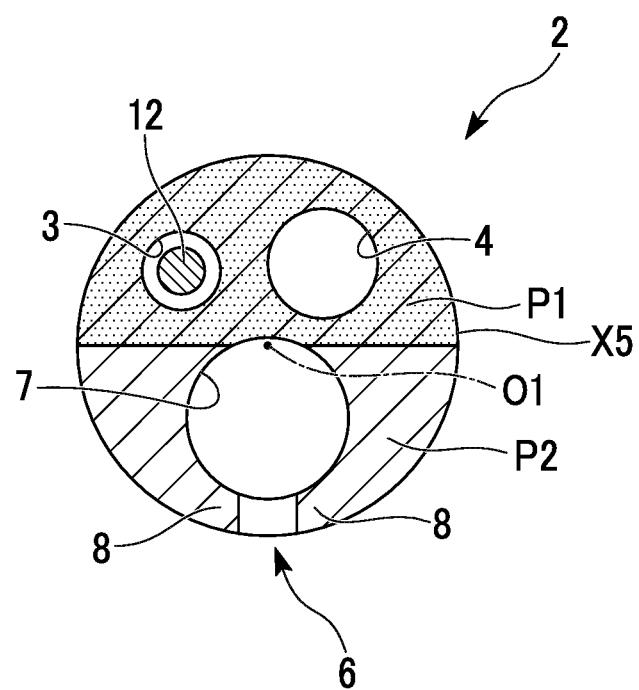
FIG. 8 is a sectional view taken along line E-E of FIG. 5.
Figure 9:
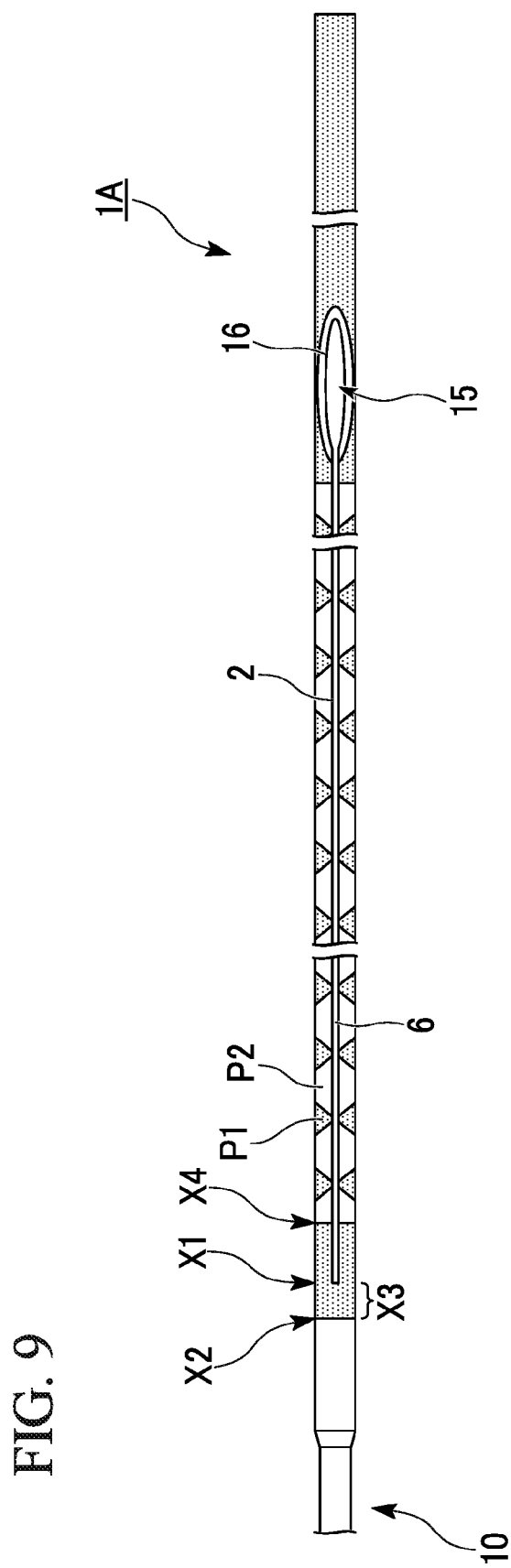
FIG. 9 is a bottom view showing a part of the catheter according to the second embodiment of the present invention.

Next, a second embodiment of the catheter of the present invention will be described. FIG. 5 is a side view showing a catheter 1A of a second embodiment of the present invention. FIG. 6 is a sectional view taken along line C-C of FIG. 5. FIG. 7 is a sectional view taken along line D-D of FIG. 5. FIG. 8 is a sectional view taken along line E-E of FIG. 5. FIG. 9 is a bottom view showing a part of the same catheter 1A.

As shown in FIGS. 5 to 9, the catheter 1A of the present embodiment has an edge section 8, a portion of which is cross-linked. That is, in the present embodiment, the edge section 8 is provided with a cross-linked section P1 and an uncross-linked section P2.

To be specific, as shown in FIG. 5, in the catheter 1A, when a elongate member 2 is viewed in a direction D1 (see FIG. 6) of a straight line that is perpendicular to a straight line L connecting an opening of a slit section 6 and the opposite side of the opening in a radial direction of the elongate member 2 and extends in the radial direction of the elongate member 2, a projected area of a portion at which a thermoplastic resin is cross-linked at the edge section 8 is smaller than that of a portion at which the thermoplastic resin is cross-linked except the edge section 8 within a range in which the edge section 8 is provided in a direction of a longitudinal axis O1 of the elongate member 2.

Such a constitution also produces the same effect as in the first embodiment.

In the catheter 1A according to the present embodiment, the opening is not easy to open because the portion that is cross-linked at the edge section 8 is relatively high in hardness, but a portion that is in an uncross-linked state at the edge section 8 is easily opened because it is relatively soft. For this reason, attaching of a guide wire to or detaching a guide wire from the slit section 6 begins at the uncross-linked portion of the edge section 8. Thereby, the guide wire is easily attached to and detached from the slit section 6.

According to the present embodiment, since adjustment of the hardness of the edge section 8 is performed by adjustment of cross-linking conditions, the catheter 1A can be manufactured such that a magnitude of a force required to attach the guide wire to or detach the guide wire from the slit section 6 is easily adjustable.

Third Embodiment

Figure 10:
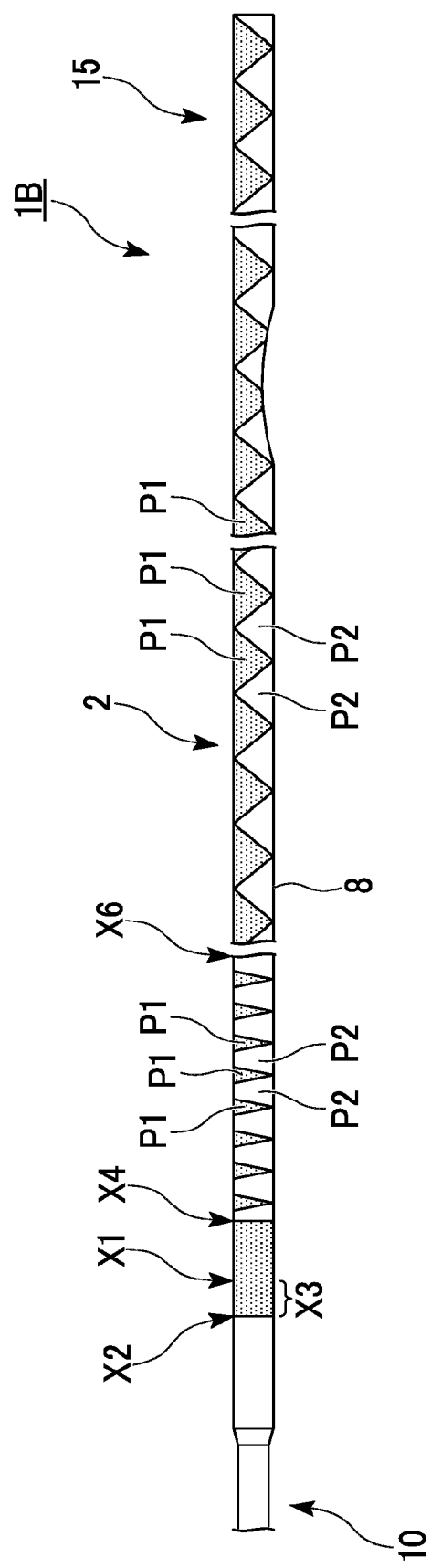
FIG. 10 is a side view showing a catheter according to a third embodiment of the present invention.
Figure 11:
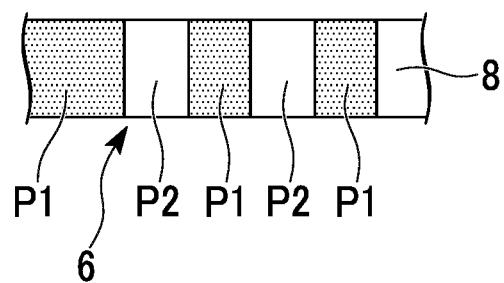
FIG. 11 is a side view showing a modification of the catheter according to the third embodiment of the present invention.
Figure 12:
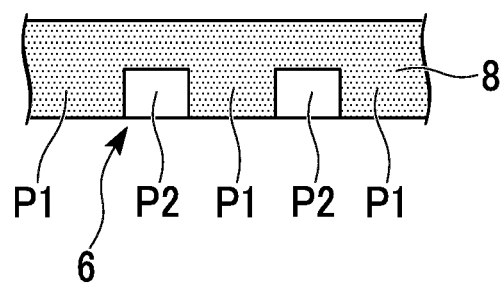
FIG. 12 is a side view showing another modification of the catheter according to the third embodiment of the present invention.
Figure 13:
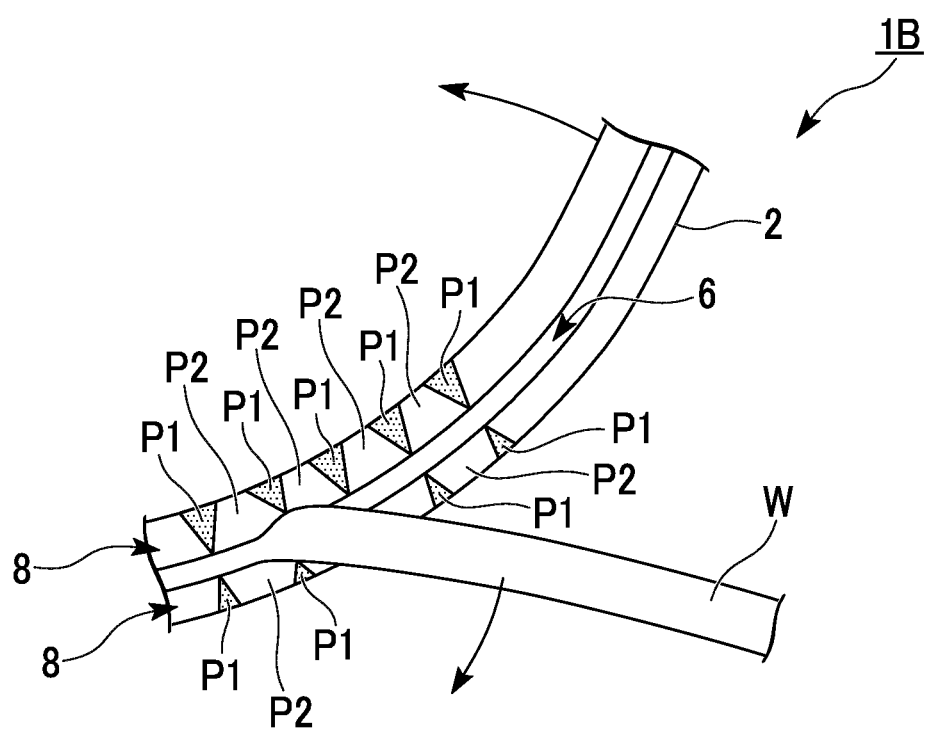
FIG. 13 is a view for describing an operation of the catheter according to the third embodiment of the present invention.

Next, a third embodiment of the catheter of the present invention will be described. FIG. 10 is a side view showing a catheter 1B of a third embodiment of the present invention. FIG. 11 is a side view showing a modification of the same catheter 1B. FIG. 12 is a side view showing another modification of the same catheter 1B. FIG. 13 is a view showing an operation of the same catheter 1B.

The catheter 1B of the present embodiment has a means of indicating a positional relation between the catheter 1B and a guide wire when the guide wire is detached from the catheter 1B to an operator who manipulates the catheter 1B.

In a process of detaching the guide wire from a slit section 6 toward a distal end from a proximal end of a elongate member 2, the catheter 1B of the present embodiment alerts the operator that the guide wire arrives in the vicinity of the distal end of the elongate member 2 using vibration transmitted via the guide wire.

To be specific, as shown in FIG. 10, in the catheter 1B of the present embodiment, an edge section 8 has a predetermined cross-linked pattern in which cross-linked sections P1 and uncross-linked sections P2 are alternately lined up in a direction of a longitudinal axis O1 of the elongate member 2 in a region from a boundary X1 between a guide wire lumen 5 and the slit section 6 to a proximal end side by a predetermined length. Also, in the present embodiment, when the elongate member 2 is viewed in a direction D1 of a straight line that is perpendicular to a straight line L connecting an opening of the slit section 6 and the opposite side of the opening in a radial direction of the elongate member 2 and extends in the radial direction of the elongate member 2, the cross-linked sections P1 are formed in a wedge section shape that is gradually reduced toward the opening in a region from a position X4 of the proximal end side by a predetermined distance from the boundary X1 between the guide wire lumen 5 and the slit section 6 to a position X6 of the proximal end side by a predetermined distance. Also, the cross-linked sections P1 have a first pattern in which they are provided in parallel at intervals in the direction of the longitudinal axis O1 of the elongate member 2.

In addition, in the present embodiment, when the elongate member 2 is viewed in the direction D1 of the straight line that is perpendicular to the straight line L connecting the opening of the slit section 6 and the opposite side of the opening in the radial direction of the elongate member 2 and extends in the radial direction of the elongate member 2, the cross-linked sections P1 have a second pattern in which wedge section shapes, each of which is gradually reduced toward the opening, are provided in parallel in the direction of the longitudinal axis O1 of the elongate member 2 in a region of a proximal end side of the elongate member 2 to the position X6.

Each distance between the cross-linked sections P1 may be set to, for instance, 20 mm in the region from the position X4 of the proximal end side by the predetermined distance from the boundary X1 between the guide wire lumen 5 and the slit section 6 to the position X6 of the proximal end side by the predetermined distance.

Alternatively, instead of the pattern in which the cross-linked sections P1 and the uncross-linked sections P2 are alternately lined up in the direction of the longitudinal axis O1 of the elongate member 2, the edge section 8 may have a pattern in which regions having a high cross-linking degree and regions having a low cross-linking degree are alternately lined up in the direction of the longitudinal axis O1 of the elongate member 2.

In addition, as shown in FIGS. 11 and 12, if the cross-linked sections P1 and the uncross-linked sections P2 are alternately disposed at the edge section 8, cross-linking conditions of the other portions may be appropriately set in the present embodiment.

In the present embodiment, in the cross-linked sections P1 and the uncross-linked sections P2 of the edge section 8, an amount of force required to detach the guide wire through the opening has a difference according to a difference in hardness. The cross-linked sections P1 and the uncross-linked sections P2 of the edge section 8 are alternately provided in the direction of the longitudinal axis O1 of the elongate member 2. For this reason, the amount of force required to detach the guide wire through the opening of the slit section 6 is relatively increased when the guide wire passes through the cross-linked sections P1 in a process in which the guide wire is detached toward the distal end side of the elongate member 2 in the direction of the longitudinal axis O1 of the elongate member 2, and is relatively reduced when the guide wire passes through the uncross-linked sections P2. That is, as shown in FIG. 13, the guide wire W alternately passes through the cross-linked sections P1 and the uncross-linked sections P2 at the edge section 8. Thereby, the amount of force required to detach the guide wire W from the slit section 6 is alternately changed.

The change of the amount of force required to detach the guide wire W from the slit section 6 is perceived as vibration of the guide wire by an operator who detaches the guide wire. The fact that the guide wire approaches a distal end of the slit section 6 before the guide wire reaches the distal end of the slit section 6 can be conveyed to the operator as the vibration of the guide wire and vibration of the catheter 1B. For this reason, it is possible to provide a chance for the operator to relax before the guide wire eats into the distal end of the slit section 6, and to prevent the distal end of the slit section 6 from being torn.

Even when the region from the boundary X1 between the guide wire lumen 5 and the slit section 6 to the proximal end side position X6 by the predetermined length has a pattern similar to the wedge-shaped pattern as in the aforementioned second embodiment, if the cross-linked sections P1 are separated at the edge section 8, an effect of conveying the vibration to the operator is produced.

Although preferred embodiments of the present invention have been described, the present invention is not limited to these embodiments. Additions, omissions, substitutions, and other modifications of the constitution are possible without departing from the spirit of the present invention. The present invention is not limited to the aforementioned description, and is only limited by the appended claims.

What is claimed is:

1. A catheter comprising:
    an elongate member configured to have a longitudinal axis, the elongate member being formed of a thermoplastic resin;
    an elongate guide wire holder section configured to include a cavity into which a guide wire is insertable at an interior of the elongate member;
    a cross-linked section configured to have a high cross-linked section and a low cross-linked section which is adjacent to the high cross-linked section in a radial direction of the elongate member and in which a cross-linking degree is lower than a cross-linking degree of the high cross-linked section, the cross-linked section being configured to extend from a distal end to a proximal end of the guide wire holder; and
    an opening section configured to communicate with the cavity of the guide wire holder and an outer circumferential surface of the guide wire holder in the low cross-linked section of the cross-linked section, the opening section being formed in a slit shape along the longitudinal axis of the guide wire holder.

2. The catheter according to claim 1, wherein:
    the elongate member includes a distal end section that is adjacent to the opening section and extends from a distal end edge of the opening section to a proximal side;
    the distal end section has the guide wire lumen that communicates with the guide wire holder and extends from the distal end edge of the opening section to the proximal side; and the high cross-linked section is formed at the distal end edge of the opening section and adjacent to the distal end edge of the opening section.

3. The catheter according to claim 1, further comprising:
a guide wire lumen formed along the longitudinal axis to insert the guide wire into the elongate member at a distal end portion of the elongate member; and
an edge section configured to communicate with the guide wire lumen, the edge section being disposed at a proximal end of the guide wire lumen, the edge section being configured to form the opening section of the slit shape along the longitudinal axis in an outer circumferential surface of the elongate member, the edge section being continuously formed along the longitudinal axis, and the edge section being configured to protrude from a position facing an edge of the opening section toward a mutually approaching direction, wherein:
a width of the opening section is smaller than or equal to a diameter of the guide wire in a state in which no external force is applied to the edge section, and the width of the opening section is passively changed by elastic deformation of the thermoplastic resin of the edge section; and
a portion located at a side opposite to the opening section in the radial direction of the elongate member is configured in such a manner that the cross-linking degree of the thermoplastic resin is higher than a cross-linking degree of the edge section.

4. The catheter according to claim 3, wherein the edge section, which is within a range from the proximal end of the guide wire lumen to a proximal end side of the elongate member by a predetermined length, is configured in such a manner that the high cross-linked section and the low cross-linked section are alternately disposed in a direction of the longitudinal axis of the elongate member.

5. The catheter according to claim 3, wherein, when the elongate member is viewed in a direction of a straight line that is perpendicular to a straight line connecting the opening section and a side opposite to the opening section in the radial direction of the elongate member and extends in the radial direction of the elongate member, a projected area of a portion at which the thermoplastic resin is cross-linked at the edge section is smaller than a projected area of a portion at which the thermoplastic resin is cross-linked except the edge section, within a range in which the edge section is provided in the direction of the longitudinal axis of the elongate member.

6. The catheter according to claim 3, further comprising:
regions in which a crosslinking agent is uncross-linked throughout a circumference of the elongate member in a circumferential direction of the elongate member and which have a length in the direction of the longitudinal axis of the elongate member; and
regions in which the elongate member is cross-linked are alternately provided in the direction of the longitudinal axis at part of the distal end portion of the elongate member within a range in which the opening section is provided in the direction of the longitudinal axis of the elongate member.

7. The catheter according to claim 3, wherein a protecting section, in which a crosslinking agent is cross-linked and which has a higher hardness than when the crosslinking agent is not cross-linked, is provided adjacent to a boundary between the guide wire lumen and the opening section in a direction of the longitudinal axis of the elongate member.

8. The catheter according to claim 7, wherein the protecting section is provided to be connected from a position of a distal end side of the elongate member relative to the boundary between the guide wire lumen and the opening section to a position of a proximal end side of the elongate member relative to the boundary.

* * * * *